US010964430B2

(12) United States Patent
Willard et al.

(10) Patent No.: US 10,964,430 B2
(45) Date of Patent: Mar. 30, 2021

(54) SYSTEM AND METHOD FOR DETERMINING COMPUTER SYSTEM COMPATIBILITY

(71) Applicant: Surescripts LLC, Arlington, VA (US)

(72) Inventors: Keith Willard, Saint Paul, MN (US); Brad Simons, Rosemount, MN (US)

(73) Assignee: Surescripts LLC, Arlington, VA (US)

(*) Notice: Subject to any disclaimer, the term of this patent is extended or adjusted under 35 U.S.C. 154(b) by 1164 days.

(21) Appl. No.: 15/153,147

(22) Filed: May 12, 2016

(65) Prior Publication Data
US 2017/0329921 A1    Nov. 16, 2017

(51) Int. Cl.
*G16H 40/63* (2018.01)
*G16H 40/67* (2018.01)
*G06F 9/445* (2018.01)

(52) U.S. Cl.
CPC .......... *G16H 40/63* (2018.01); *G16H 40/67* (2018.01); *G06F 9/44505* (2013.01)

(58) Field of Classification Search
CPC .. G06F 19/3418; G06F 19/00; G06F 9/44505; G16H 40/63
See application file for complete search history.

(56) References Cited

U.S. PATENT DOCUMENTS

| | | | | |
|---|---|---|---|---|
| 9,177,319 | B1* | 11/2015 | Chheda | G06Q 10/06 |
| 2004/0054690 | A1* | 3/2004 | Hillerbrand | G06Q 10/06 |
| 2008/0046292 | A1* | 2/2008 | Myers | G06Q 50/24 |
| | | | | 705/3 |
| 2010/0274823 | A1* | 10/2010 | Sathish | H04L 67/02 |
| | | | | 707/810 |
| 2011/0072153 | A1* | 3/2011 | Candelaria | H04L 69/18 |
| | | | | 709/237 |
| 2012/0246318 | A1* | 9/2012 | Mohammed | G06F 9/5061 |
| | | | | 709/226 |
| 2013/0030827 | A1* | 1/2013 | Snyder | G06F 19/324 |
| | | | | 705/2 |
| 2013/0325789 | A1* | 12/2013 | Krishnan | G06F 16/254 |
| | | | | 707/602 |
| 2014/0310683 | A1* | 10/2014 | McCarty | G06F 8/20 |
| | | | | 717/105 |

(Continued)

*Primary Examiner* — Umar Cheema
*Assistant Examiner* — James Ross Hollister
(74) *Attorney, Agent, or Firm* — Fiala & Weaver P.L.L.C.

(57) ABSTRACT

Systems and methods, as well as devices, are described for computer system compatibility. Computer systems exchange messages over a network or communication link according to a communication standard. A declarations of how a communication standard is implemented by a trading partner computer system is received by a host provider computer system, and an ontology model of the implementation is generated based at least in part on information in the declaration. The ontology models are queried to cause the provision of query responses indicative of differences between the trading partner implementation and a host provider implementation of the communication standard. Indications of communication compatibility between the computer systems are generated based on results of the queries against the ontology model. The indications may include augmented enforcement libraries to be implemented by the trading partner for messaging interoperability.

20 Claims, 5 Drawing Sheets

(56) References Cited

U.S. PATENT DOCUMENTS

| | | | |
|---|---|---|---|
| 2015/0100787 A1* | 4/2015 | Westin | G06F 21/602 |
| | | | 713/168 |
| 2016/0019294 A1* | 1/2016 | Dong | G06F 16/288 |
| | | | 707/794 |
| 2016/0019346 A1* | 1/2016 | Boston | G16H 10/60 |
| | | | 705/3 |
| 2016/0063191 A1* | 3/2016 | Vesto | G06F 19/324 |
| | | | 705/2 |
| 2016/0210427 A1* | 7/2016 | Mynhier | G16H 10/60 |
| 2017/0103163 A1* | 4/2017 | Emanuel | G06F 16/23 |
| 2017/0270532 A1* | 9/2017 | Livesay | G16H 10/60 |

* cited by examiner

SYSTEM AND METHOD FOR DETERMINING COMPUTER SYSTEM COMPATIBILITY

BACKGROUND

I. Technical Field

The present subject matter relates to communication compatibility between computer systems over a communication link.

II. Background Art

Fast Healthcare Interoperability Resources (FHIR) is a recent standard for clinical messaging in which healthcare information is conveyed electronically (see https://www.hl7.org/fhir/overview.html). FHIR provides, at its base level, a certain degree of specificity for fundamental atoms of information in clinical messaging, but FHIR leaves parts of the standard optional or "loose." This "looseness" is constrained at runtime for message composition and transmission, and is dependent on the specific use cases and information exchange partners.

The basic FHIR standard allows for specific profiles of information to be used by different entities. For instance, this allows a trading partner to declare what constraints are used at runtime, such as the names and types of extension fields that are not defined or not required in the base standard, the narrowing of cardinality restrictions on base element definitions, and the naming (i.e., the binding) of dictionary related elements to a specific named dictionary (e.g., a general code element can be "bound" to a specific coding dictionary such as the International Classification of Diseases, tenth revision (ICD-10) (see http://www.who.int/classifications/icd/en/)).

Accordingly, two different trading partners can both be using the FHIR standard correctly, yet not be able to actually interoperate and exchange clinical messaging with each other due to incompatibilities based on their respective use of extensions, definitions, cardinality, bindings, and/or the like.

BRIEF SUMMARY

Methods, systems, and apparatuses are described for communication compatibility between computer systems, substantially as shown in and/or described herein in connection with at least one of the figures, as set forth more completely in the claims.

BRIEF DESCRIPTION OF THE DRAWINGS/FIGURES

The accompanying drawings, which are incorporated herein and form a part of the specification, illustrate embodiments and, together with the description, further serve to explain the principles of the embodiments and to enable a person skilled in the pertinent art to make and use the embodiments.

Embodiments will now be described with reference to the accompanying drawings. In the drawings, like reference numbers indicate identical or functionally similar elements. Additionally, the left-most digit(s) of a reference number identifies the drawing in which the reference number first appears.

DETAILED DESCRIPTION

I. Introduction

Figure 1:
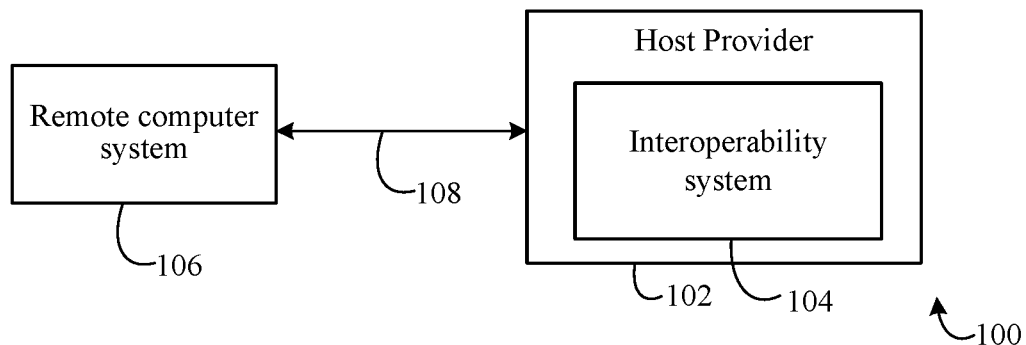
FIG. 1 shows a block diagram of a network of computer systems that includes an interoperability system, according to an example embodiment.

The present specification discloses numerous example embodiments. The scope of the present patent application is not limited to the disclosed embodiments, but also encompasses combinations of the disclosed embodiments, as well as modifications to the disclosed embodiments.

References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

In the discussion, unless otherwise stated, adjectives such as "substantially," "approximately," and "about" modifying a condition or relationship characteristic of a feature or features of an embodiment of the disclosure, are understood to mean that the condition or characteristic is defined to be within tolerances that are acceptable for operation of the embodiment for an application for which it is intended.

Furthermore, it should be understood that spatial descriptions (e.g., "above," "below," "up," "left," "right," "down," "top," "bottom," "vertical," "horizontal," etc.) used herein are for purposes of illustration only, and that practical implementations of the structures described herein can be spatially arranged in any orientation or manner.

Still further, it should be noted that the drawings/figures are not drawn to scale unless otherwise noted herein.

Numerous exemplary embodiments are now described. Any section/subsection headings provided herein are not intended to be limiting. Embodiments are described throughout this document, and any type of embodiment may be included under any section/subsection. Furthermore, it is contemplated that the disclosed embodiments may be combined with each other in any manner. That is, the embodiments described herein are not mutually exclusive of each other and may be practiced and/or implemented alone, or in any combination.

II. Example Embodiments

The example techniques and embodiments described herein may be adapted to various types of systems and devices, for example but without limitation, computing systems (e.g., computers/computing devices such as desktops, laptops, etc., and servers, enterprise computing systems, etc.), communication devices (e.g., cellular and smart phones, etc.), and/or the like, that communicate information, such as in accordance with communication standards. For instance, computing systems that communicate over a network and exchange clinical messages in accordance with the FHIR standard may be configured according to the described embodiments and techniques. While the embodiments herein may be described with respect to various computing systems and implementations as conceptual and/or illustrative examples for descriptive consistency, other types of electronic and communication devices and implementations are also contemplated for implementing the disclosed techniques. It is contemplated herein that in various embodiments and with respect to the illustrated figures of this disclosure, one or more components described and/or shown may not be included and that additional components may be included.

The example techniques and embodiments described herein provide for communication compatibility between computer systems, e.g., such as compatibility for clinical messaging over a network between computer systems including, but not limited to, clinical messaging according to the FHIR standard. The computer systems may be a host entity, a trading partner(s), and/or another third-party entity(ies) (and in the descriptions herein a trading partner may be a third-party entity). The FHIR standard was promulgated to provide a communication protocol with a certain degree of specificity for fundamental atoms of information in clinical messaging, although FHIR leaves parts of the standard optional or "loose." This "looseness" is constrained at runtime for message composition and transmission, and is dependent on the specific use cases and information exchange partners. FHIR provides a communication protocol to exchange clinical information. That is, messaging between computer systems using FHIR includes the exchange of clinical information that may relate to a number of defined "resources" associated with patients, practitioners, appointments, clinical observations, clinical documents, medications, accounts, and/or the like, as defined by the FHIR standard. For instance, an FHIR patient resource may include information about a patient like patient name, address, title, contact information, age, gender, etc. An FHIR resource also utilizes libraries with objects that represent the resource. Generally, FHIR resources also include metadata (e.g., in formats such as, but without limitation, extensible markup language (XML) format) that describes different aspects of the resources to characterize what is allowed by the standard. That is, the metadata may describe the structure and components of the resource (e.g., properties of the resource such as, but not limited to, a first property for a resource being an identification field, while a second property for the resource is a patient's last name, and a third property for the resource is a patient's first name, etc.), rather than actual informational values associated the resource (e.g., Resource ID=123456, Last name="Rose", and First name="Robert").

Entities such as a host entity, a trading partner, and/or another third-party entity may implement attributes of a communication standard or protocol, e.g., under the FHIR standard, differently than other entities. Standard/Protocol implementations may be advertised by entities in declarations that describe such implementations, including their variations. That is, different definitions, extensions (e.g., using formal guidelines), metadata, bindings, cardinality, and libraries for resources, that are represented in respective declarations may be implemented by entities. These differences may also result in or include semantic differences from other implementations (i.e., semantic characteristics) utilized by other entities. In some cases, these differences result in communication incompatibilities between communicating entities. Furthermore, communication incompatibilities between communicating entities may not manifest in every communication message which creates a network-/Internet-centric problem for being able to root-cause communication issues between communicating entities messaging over a network and/or the Internet according to a communication standard/protocol such as FHIR.

As described herein with respect to embodiments, clinical information may be exchanged between computer systems by including such information in messages as exemplarily noted above, e.g., according to the FHIR standard. Regarding the network-/Internet-centric problem previously-noted, consider an example where a trading partner implements an optional aspect of the FHIR standard (e.g., an optional extension) that is not supported by a host provider, or would result in a communication incompatibility with the host provider. Given the optional nature of the extension, not every message transmitted by the trading partner activates the optional extension. For instance, the trading partner could provide messages without the optional extension activated for an extended period of time without communication compatibility issues if the optional extension is dormant in the transmitted messages. At a later time, however, the trading partner may activate the optional extension in a message that results in an unexpected communication compatibility issue when the host provider receives the message and is unable to consume it.

The described techniques and embodiments provide systems, methods, and devices to receive, or in some embodiments receive by retrieving, declarations representative of how a computer system implements a communication standard/protocol for messaging the clinical information, and to generate an indication of communication compatibility between communicating computer systems based at least in part on the declarations. That is, according to techniques and embodiments, FHIR declarations related to the characteristics of trading partners (and third-party entities) FHIR capabilities are consumed by a host provider and core metadata information therein is transformed into a general modeling language, e.g., resource description framework (RDF), to generate an RDF ontology model, i.e., a structured implementation for trading partners. The core metadata is augmented with knowledge of which FHIR base- and extension-components and parts are important or required for success in interacting with given host provider FHIR transaction services, as well as other trading partners. The described interoperability systems and devices for generating indications of communication compatibility predict compatibility against the general ontological model to determine if a given trading partner will successfully be able to semantically interoperate in a network model that includes the host provider and other conformant trading partners. In embodiments, it is contemplated that one or more declarations each having one or more standard/protocol resources represented therein, may be included in the described generation of indications of communication compatibility.

Utilizing a combination of a general model of a standard/protocol, e.g., an RDF model thereof, along with messaging information, that forms a basis for a standard/protocol ontology model of a trading partner, and the generation of a combination of constrained queries over the ontology model, programmatic code allows for a determination of either predicted communication compatibility, or the predicted interoperability or the specific prediction of non-interoperability and the specific cause of the lack of interoperability, according to the described techniques and embodiments herein.

For instance, in FIG. 1, a block diagram of a network of computer systems 100 that includes an interoperability system is shown, according to an embodiment. Network of computer systems 100 includes a host provider 102, an interoperability system 104, and a remote computer system 106. Host provider 102 may be communicatively coupled or linked to remote computer system 106 via a communication link 108.

Host provider 102 may comprise one or more computers/servers of a host entity facilitating access to interoperability system 104 by remote computer systems such as remote computer system 106, according to embodiments. Host provider 102 may include geographically distributed computers/servers, a rack server system(s), a stand-alone server, etc.

Remote computer system 106 may comprise one or more computers/servers of an entity, such as a trading partner and/or third-party entity, that desires to exchange information in the form of messages (e.g., clinical information in messages according to the FHIR standard) with host provider 102 over communication link 108.

Communication link 108 may comprise at least one network or direct communication connection, or any combination thereof, between host provider 102 and remote computer system 106 that enables communication messages and declarations, as described herein, to be exchanged. As used herein, the term "messages" includes resources, data, information, packets, and/or the like, related to messaging such as clinical messaging, transmitted and/or received according to any communication standard or protocol, or according to ad hoc communications. In embodiments, communication link 108 may comprise wired and/or wireless portions.

Interoperability system 104 may comprise hardware and/or software components configured to automatically generate an indication of communication compatibility between computer systems, as described herein. For instance, in embodiments, interoperability system 104 is configured to automatically generate an indication of communication compatibility between host provider 102 and remote computer system 106. Interoperability system 104 is configured to perform this function by automatically generating an ontology model (e.g., through RDF) based on information in the declaration from remote computer system 106 and a standard model of a messaging protocol or standard implementation (e.g., FHIR) used by host provider 102 (e.g., through RDF). The ontology model is a uniform model for any given remote computer system, as described herein, and provides a characterization of how remote computer systems utilize messaging protocols or standards. The ontology model is automatically queried by interoperability system 104 to determine query responses indicative of differences, if any, in implementations of messaging protocols or standards between host provider 102 and remote computer system 106. Interoperability system 104 is configured to automatically generate and provide indications of compatibility, as well as indications of incompatibility that may include reasons for/analyses of communication inoperability, enumerated recommendations or required changes to be made for compatibility, and/or augmented enforcement libraries as described below, according to embodiments.

Interoperability system 104 is also configured to automatically cause activation of a communication interface (not shown but described elsewhere herein) to execute functionality thereof and provide the indication(s) to remote computer system over communication link 108.

It is contemplated herein, according to embodiments, that host provider 102 and interoperability system 104 may together comprise one or more servers that perform the described functionality of interoperability system 104, as well as other functionality for a host entity, or may be a single server performing either or both of these types of functionality. Other relational configurations of host provider 102 and interoperability system 104 are also contemplated herein, as would be understood by a person of skill in the relevant art(s) having the benefit of this disclosure.

Figure 2:
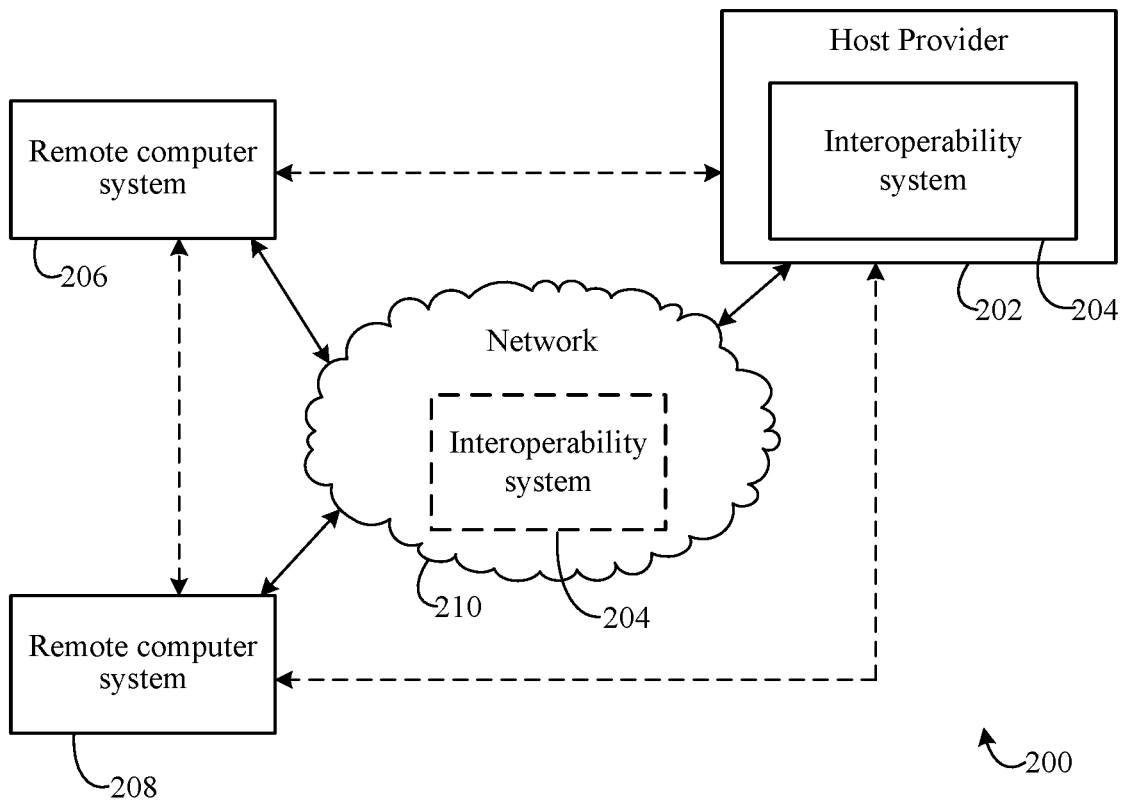
FIG. 2 shows a block diagram of a network of computer systems that includes an interoperability system, according to an example embodiment.

Turning now to FIG. 2, a block diagram of a network of computer systems 200 that includes an interoperability system is shown, according to an embodiment. Network of computer systems 200 may be a further embodiment of network of computer systems 100 of FIG. 1. Network of computer systems 200 includes a host provider 202, an interoperability system 204, a remote computer system 206, and a remote computer system 208. Host provider 202, remote computer system 206, and remote computer system 208 may be communicatively coupled or linked each other via a network 210.

Host provider 202 may be a further embodiment of host provider 102 of FIG. 1, and for the purposes of illustration for FIG. 2 is configured the same, or substantially the same, as host provider 102 above. Interoperability system 204 may be a further embodiment of interoperability system 104 of FIG. 1, and for the purposes of illustration for FIG. 2 is configured the same, or substantially the same, as interoperability system 104 above. Remote computer system 206 and remote computer system 208 may each be a further embodiment of remote computer system 106 of FIG. 1, and for the purposes of illustration for FIG. 2 is configured the same, or substantially the same, as remote computer system 106 above.

Network 210 may be a further embodiment of communication link 108 of FIG. 1. Network 210 may comprise at least one network and/or direct connection (i.e., a communication link), or any combination thereof. That is, network 210 may be any combination of the Internet, the "cloud," direct communication links, business and/or enterprise networks, and/or the like.

As noted, network 210 is configured to communicatively couple host provider 202, remote computer system 206, and remote computer system 208 to each other. Accordingly, network of computer systems 200 is configured as a further embodiment of network of computer systems 100 in that interoperability system 204 is configured to automatically generate an indication of communication compatibility between any combination of host provider 202, remote computer system 206, and remote computer system 208, similarly as described above for interoperability system 104 of FIG. 1.

For instance, an example scenario is now described in the context of network of computer devices as shown in FIG. 2. Host provider 202 utilizes an implementation 'A' of a communication or messaging standard/protocol, such as FHIR as described herein, and remote computer system 206 utilizes an implementation 'B' of the same standard/protocol. Implementation 'B' may have one or more definitions, extensions, metadata, bindings, cardinality, and libraries for resources that are the same, or are different, under the standard from implementation 'A', and there may also be semantic differences between declarations in implementation 'A' and implementation 'B', etc. For instance, differences in declaration structure (that correlates to standard/protocol implementation differences) may arise due to differences in at least one of metadata, definitions, bindings, extensions, cardinality, and semantic characteristics of information.

Continuing with the example scenario, host provider 202 is associated with a host entity, and remote computer system 206 is associated with a trading partner or third-party entity that desires to exchange messaging communications with host provider 202 over network 210. To determine communication compatibility between host provider 202 and remote computer system 206, and to generate indications thereof, remote computer system 206 transmits or makes available a declaration according to implementation 'B' to host provider 202 over network 210. Interoperability system 204 of host provider 202 receives, e.g., by transmission from remote computer system 206 or via retrieval by host provider 202, the declaration from remote computer system 206 and generates an ontology model representative of characteristics associated with implementation 'B' of the standard/protocol. In an embodiment, the ontology model is based at least on metadata for a communication standard/protocol to be used in messaging. The ontology model is queried by interoperability system 204, and interoperability system 204 generates queries against the ontology model. The query responses (i.e., the query results) are utilized to generate one or more indications of communication compatibility between remote computer system 206 and host provider 202. According to embodiments, the indications of communication compatibility may include a set of incompatibility factors that represent one or more differences between implementation 'A' and implementation 'B' of the standard/protocol that prevent communication compatibility between remote computer system 206 and host provider 202. The indications may include reasons for/analyses of communication inoperability, enumerated recommendations or required changes to be made for compatibility, and/or augmented enforcement libraries as described below, according to embodiments. Interoperability system 204 then causes the activation or automatic activation of a communication interface (e.g., of interoperability system 204 and/or host provider 202) to execute functionality thereof and provide the indications to remote computer system 206 over network 210. Remote computer system 206 then receives the indications and may make recommended and/or required changes to implementation 'B' that allow for communication compatibility with host provider 202. In other words, communication compatibility includes host provider being able to consume messages from remote computer system 206 and vice versa.

It is noted that implementing recommended and/or required changes to implementation 'B' may result in this implementation being identical or substantially identical to implementation 'A', or may result in implementation 'B' remaining different from implementation 'A' while becoming compatible for communications and messaging between host provider 202 and remote computer system 206.

Further extending this example scenario, assume that remote computer system 208 now also wants to exchange messaging with host provider 202, and/or with remote computer system 206. Remote computer system 208 utilizes an implementation 'C' of the same standard/protocol and provides a declaration that may be obtained over network 210 by host provider 202 causing interoperability system 204 to generate an indication of communication compatibility for host provider 202 (and by association remote computer system 206) with remote computer system 208 as similarly described above for remote computer system 206. In this way, host provider 202 and remote computer system 208 may be configured to have compatibility in their communications, and because remote computer system 206 is also compatible with host provider 202, remote computer system 206 and remote computer system 208 also have compatibility in their communications with each other. As similarly described above for implementation 'B' and implementation 'A', implementations 'A', 'B', and 'C' may become identical or substantially identical subsequent to changes made to implementations 'C', these implementations may remain different while still being compatible for communications and messaging, or any combination of these two possibilities.

Still referring to FIG. 2, while shown for illustrative simplicity and brevity as including a single host provider (host provider 202) and two remote computer systems (remote computer systems 206/208), it is contemplated herein that network of computer systems 200 may include more or fewer of any of these components in embodiments.

The described techniques and embodiments provide for automatically determining and generating indications of communication compatibility between computer systems that are communicatively coupled to each other. The described embodiments and techniques allow for reduced development time from engineering teams of an entity for implementing messaging and communication protocols/standards in a way that not only allows communications with a host provider and other computer systems of other entities, but that also allows flexibility for entity-specific variations of communication protocols/standards when possible. The described embodiments and techniques may be configured and scaled to different messaging and communication protocols/standards, such as, but not limited to, FHIR.

Systems, devices, and apparatuses contemplated herein, such as systems, devices, and apparatuses that include interoperability systems and/or components thereof, may be configured in various ways for communication interoperability between computer systems according to the described techniques and embodiments. Techniques and embodiments are provided for implementation in and with devices, apparatuses, and systems that utilize networks to communicate with other devices, apparatuses, and systems. For instance, in embodiments, interoperability systems according to the described techniques and embodiments may be implemented in devices, apparatuses, and systems such as those enumerated herein, to determine and/or provide communication compatibility between unrelated computer systems over a communication link such as a network or the Internet and to generate indications of the communication compatibility.

The techniques and embodiments described herein provide for improvements in communication compatibility between computer systems, such as but without limitation, clinical messaging communications according to the FHIR standard.

For instance, methods, systems, circuits, devices, and apparatuses are provided for interoperability systems. An interoperability system for generating an indication of communication compatibility between a first computer system and one or more second computer systems that are connected to the first computer system via at least one network in accordance with an example aspect is described. The interoperability system includes a memory configured to store program instructions, and at least one processor configured to execute the program instructions to perform a method. The method includes receiving at least one declaration structured in accordance with a first implementation of a communication protocol from the first computer system over the at least one network, and activating a model generator responsive to receiving the at least one declaration to cause generation of an ontology model by the model generator that is representative of characteristics of the first implementation of the communication protocol used by the first computer system. The method also includes activating a query provider to generate at least one query and apply the at least one query against the ontology model that causes at least one query response to be provided, the at least one query being configured to determine compliance with a second implementation of the communication protocol. The method further includes generating the indication of communication compatibility based on the at least one query response, the indication of communication compatibility including a set of incompatibility factors that represent one or more differences between the first implementation of the communication protocol and the second implementation of the communication protocol that prevent communication compatibility between the first computer system and the one or more second computer systems.

In embodiments, the method of the interoperability system includes responsive to generating the indication of communication compatibility, causing activation of a communication interface to provide the indication to the first computer system over the at least one network.

In embodiments, the communication protocol is FHIR, and generating the indication comprises generating at least one augmented enforcement library associated with the FHIR protocol. The set of incompatibility factors comprises one or more extension factors indicative of extension implementation in the declaration, according to embodiments.

In embodiments, the ontology model comprises a resource description framework (RDF) model, and the declaration comprises at least one of metadata, extensions, definitions, bindings, cardinality, and semantic characteristics of information.

The interoperability system is included in the one or more second computer systems, or is included in a cloud-based computer system, according to various embodiments.

A method for generating an indication of communication compatibility between a first computer system and one or more second computer systems that are connected to the first computer system via at least one network in accordance with another example aspect is described. The method includes receiving at least one declaration structured in accordance with a first implementation of a communication protocol from the first computer system over the at least one network, and activating a model generator responsive to receiving the at least one declaration to cause generation of an ontology model by the model generator that is representative of characteristics of the first implementation of the communication protocol used by the first computer system. The method also includes activating a query provider to generate at least one query and apply the at least one query against the ontology model that causes at least one query response to be provided, the at least one query being configured to determine compliance with a second implementation of the communication protocol. The method further includes generating the indication of communication compatibility based on the at least one query response, the indication of communication compatibility including a set of incompatibility factors that represent one or more differences between the first implementation of the communication protocol and the second implementation of the communication protocol that prevent communication compatibility between the first computer system and the one or more second computer systems.

In embodiments, the communication protocol is FHIR, and generating the indication comprises generating at least one augmented enforcement library associated with the FHIR protocol. The set of incompatibility factors comprises one or more extension factors indicative of extension implementation in the declaration.

In embodiments, the ontology model comprises an RDF model, and the declaration structure comprises at least one of metadata, extensions, definitions, bindings, cardinality, and semantic characteristics of information.

The method is performed by an interoperability system that is included in the one or more second computer systems, or is included in a cloud-based computer system, according to various embodiments.

A computer readable storage medium encoded with program instructions that, when executed by a computing device, cause the computing device to perform a method for generating an indication of communication compatibility between a first computer system and one or more second computer systems that are connected to the first computer system via at least one network in accordance with yet another example aspect is also described. The program instructions include model generator logic, query provider logic, and compatibility logic. The model generator logic is activated responsive to receiving at least one declaration structured in accordance with a first implementation of a communication protocol from the first computer system over the at least one network to cause generation of an ontology model by the model generator that is representative of characteristics of the first implementation of the communication protocol used by the first computer system. The query provider logic is activated responsive to generation of the ontology model to generate at least one query and apply the at least one query against the ontology model that causes at least one query response to be provided, the at least one query being configured to determine compliance with a second implementation of the communication protocol. The compatibility logic generates the indication of communication compatibility between the first computer system and the one or more second computer systems based on the at least one query response.

In embodiments, the indication of communication compatibility includes a set of incompatibility factors that represent one or more differences between the first implementation of the communication protocol and the second implementation of the communication protocol that prevent communication compatibility between the first computer system and the one or more second computer systems. The set of incompatibility factors comprises one or more extension factors indicative of extension implementation in the declaration, according to embodiments, the communication protocol may be FHIR, and the ontology model comprises an RDF model.

Various example embodiments are described in the following subsections. In particular, example interoperability system embodiments are described, followed by example ontology model embodiments, including RDF implementations. Next, further example embodiments and advantages are described, and subsequently example processing device embodiments are described. Finally, some concluding remarks are provided.

III. Example Interoperability System Embodiments

As noted above, embodiments for systems and devices may be configured to perform their functions and operations (e.g., methods) in various ways, and it is contemplated herein that in various embodiments, one or more components described and/or shown may not be included and that additional components may be included.

Figure 3:
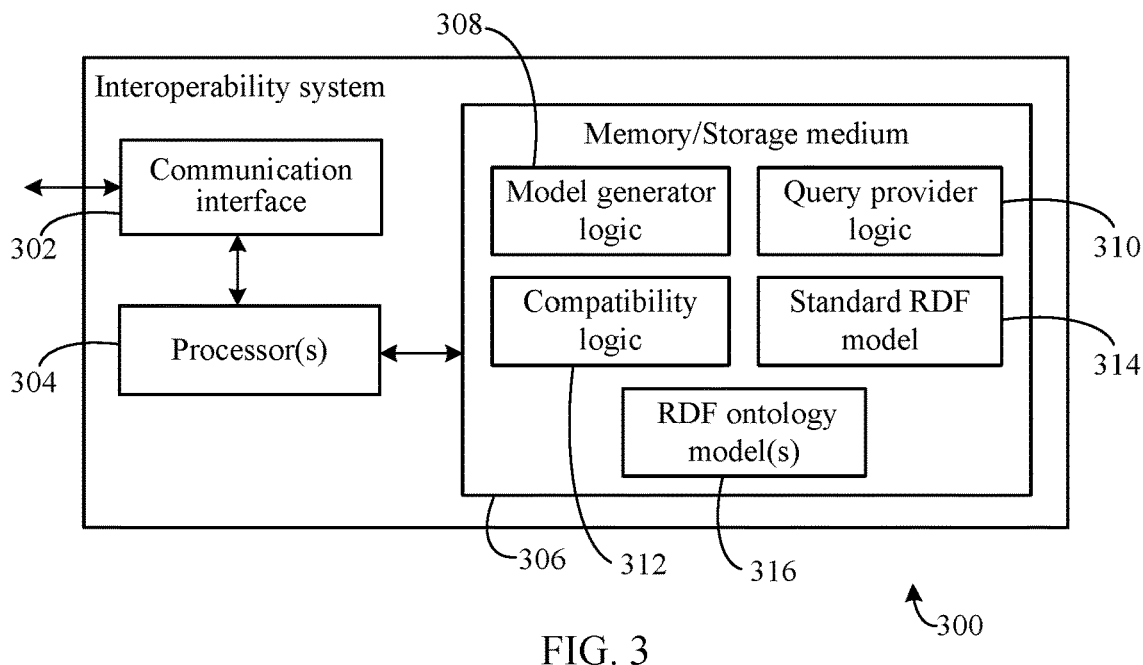
FIG. 3 shows a block diagram of an interoperability system, according to an example embodiment.

Turning now to FIG. 3, a block diagram of an interoperability system 300 is shown, according to an embodiment. Interoperability system 300 may be a further embodiment of interoperability system 104 of FIG. 1 and/or interoperability system 204 of FIG. 2. That is, interoperability system 300 may be included or implemented in a host provider that is communicatively coupled to one or more remote computer systems over a communication link or network, as described above.

Interoperability system 300 includes a communication interface 302, one or more processors ("processor") 304, and a memory/storage medium ("memory") 306. Processor 304 is communicatively coupled to communication interface 302 and to memory 306. Communication interface 302 is configured to be communicatively coupled to a communication link and/or to a network, such as communication link 108 of FIG. 1 and/or network 210 of FIG. 2.

Communication interface 302 may be one or more interfaces, such as hardware network interfaces, that are configured to transmit and/or receive communications and messages, as well as declarations, over a network or communication link as described herein. Processor 304 may be one or more computer processors or processing devices as known to one of skill in the relevant art(s) having the benefit of this disclosure, such as those configured to operate in a computer, a server, a computing systems, and/or the like, as described herein. Processor 304 is configured to execute computer program instructions to perform the described communication compatibility functions and methods.

Memory 306 is a hardware device(s) of, or associated with, a computer, a server, a computing system, and/or the like, as described herein, that is configured to store computer program instructions that may be executed by processor 304. For example, as shown in FIG. 3, memory 306 is configured to store model generator logic 308, query provider logic 310, and compatibility logic 312. Memory 306 is also configured to store a standard RDF model 314 and an RDF ontology model 316. In embodiments, one or more of standard RDF model 314 and RDF ontology model 316 may not be stored at all times in memory 306, but may be stored upon generation thereof, as described herein. It is also contemplated herein that in embodiments, standard RDF model 314 and RDF ontology model 316 may respectively be a model and an ontology model based on a framework or data structure implementation other than RDF. Memory 306 is also configured to store declarations and/or messages, such as messages with clinical information, from remote computer systems received by communication interface 302.

Figure 4:
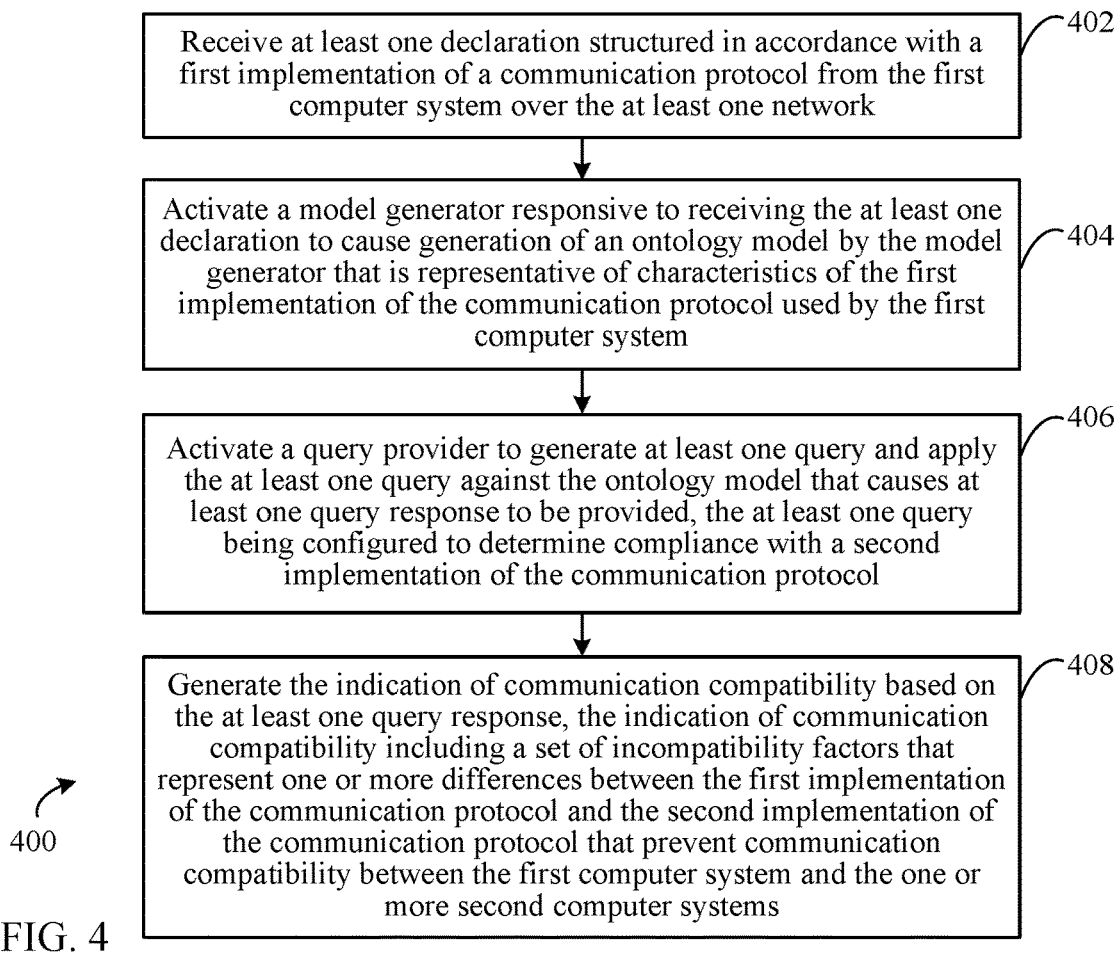
FIG. 4 shows a flowchart of a method for determining and providing communication compatibility between computer systems, according to an example embodiment.

In FIG. 4, a flowchart 400 for determining and providing communication compatibility between computer systems is shown, according to an embodiment. That is, flowchart 400 may exemplify a method performed in a computing system for generating an indication of communication compatibility between a first computer system and one or more second computer systems that are connected to the first computer system via at least one network. Example techniques and embodiments described herein may be configured and/or implemented to perform various aspects of communication compatibility determination and provision according to flowchart 400. For instance, interoperability system 104 of FIG. 1, interoperability system 204 of FIG. 2, and/or interoperability system 300 of FIG. 3, along with any of their respective subcomponents, may perform functions according to flowchart 400 of FIG. 4. Flowchart 400 is described as follows in the context of interoperability system 300 of FIG. 3 for exemplary illustration.

At least one declaration structured in accordance with a first implementation of a communication protocol is received from the first computer system over the at least one network (402). For example, a declaration from a remote computer system may be received over a network by communication interface 302 of interoperability system 300 in a host provider. The declaration may be structured according to an implementation of the FHIR standard protocols in embodiments. Communication interface 302 is configured to provide received declarations to processor 304 and/or to memory 306.

A model generator is activated responsive to receiving the at least one declaration to cause generation of an ontology model by the model generator that is representative of characteristics of the first implementation of the communication protocol used by the first computer system (404). For instance, when a declaration is received by communication interface 302 or when a declaration is provided to processor 304 and/or memory 306 from communication interface 302 (as in 402 above), processor 302 may be configured to activate a model generator to cause the model generator to generate an ontology model that corresponds to the remote computer system.

Figure 5:
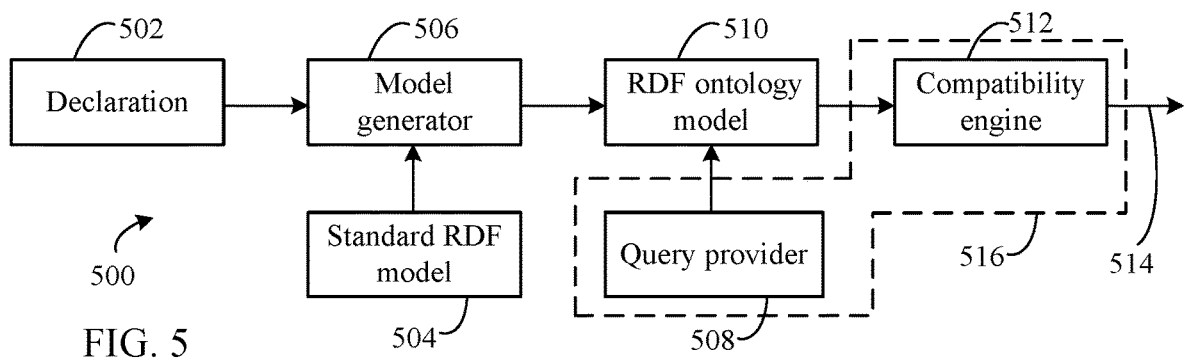
FIG. 5 shows an interoperability system execution flow, according to an example embodiment.

In FIG. 5, an interoperability system execution flow ("execution flow") 500 is shown, according to an embodiment. As illustrated in execution flow 500, a declaration 502 is provided to a model generator 506. Processor 304, described above, is configured to execute computer program instructions (i.e., computer program logic) stored in memory 306. With respect to (404), processor 304 executes model generator logic 308 stored in memory 306 to activate/execute model generator 506. Model generator 506 may be automatically activated by processor 304 responsive to receiving a declaration (as in 402), or at any other time. Model generator 506 retrieves, or is provided, a standard RDF model 504 (that may be an embodiment of standard RDF model 314 stored in memory 306). Model generator 506 generates an RDF ontology model 510 (that may be an embodiment of RDF ontology model 316 stored in memory 306) that represents characteristics of an implementation of a communication protocol, e.g., FHIR, used by the remote computer system to generate messages to be exchanged, and that is based at least in part on the received declaration, as described herein. The generated RDF ontology model 510 is based on standard RDF model 504 and information included in and/or about declaration 502. Such information includes, without limitation, metadata, definitions, extensions, bindings, cardinality, and libraries for resources under the FHIR standard associated with declaration 502, as well as semantic characteristics of declaration 502 content.

Referring back to flowchart 400, a query provider is activated to generate at least one query and apply the at least one query against the ontology model that causes at least one query response to be provided, the at least one query being configured to determine compliance with a second implementation of the communication protocol (406). For instance, processor 302 may be configured to activate a query provider to cause one or more queries to be generated. Generated queries may be applied against RDF ontology model 510 to cause query responses to be generated. The generated queries are configured to determine compliance with an implementation of the communication protocol, e.g., FHIR, utilized by a host provider, as described herein. For example, an ontology model of an implementation of a communication or messaging standard/protocol, e.g., RDF ontology model 510, may include elements of standard RDF model 504 such as representations of resources or other model-specific data structures of the standard/protocol, and also include host entity-specific implementations associated with the resources or other model-specific data structures and/or metadata for which information thereof may be included in declaration 502. Entity-specific implementations may be, but are not limited to, definitions, extensions, metadata, bindings, cardinality, and libraries for resources under the FHIR standard associated with declaration 502, as well as semantic characteristics of declaration 502 content. For instance, a query against a modeled binding or structure definition for a host entity implementation model (e.g., of host provider 202 of FIG. 2) may result in a different query response than when the same query is run against a trading partner or third-party entity implementation model (e.g., of remote computer systems 206/208 of FIG. 2).

In embodiments, processor 304 is configured to automatically activate the query provider subsequent to generation of RDF ontology model 510 by model generator 506 (as in 404), or at any other time. With reference to the execution flow 500 of FIG. 5, processor 304 executes query provider logic 310 stored in memory 306 to activate/execute query provider 510. Query provider 510 causes one or more queries to be generated (as in 406) to apply against RDF ontology model 510.

Referring again to flowchart 400, the indication of communication compatibility is generated based on the at least one query response, the indication of communication compatibility including a set of incompatibility factors that represent one or more differences between the first implementation of the communication protocol and the second implementation of the communication protocol that prevent communication compatibility between the first computer system and the one or more second computer systems (408). For example, processor 302 may be configured to activate a compatibility engine to cause one or more indications to be generated based on query responses of RDF ontology model 510 (as in 406). In embodiments, the query responses are analyzed by a compatibility engine to determine differences in responses to the queries, as well as to determine recommended or required changes for the utilization of the standard/protocol by a remote computer system in order to become compatible in exchanging messages with the host provider.

In embodiments, processor 304 is configured to automatically activate the compatibility engine responsive to generation of the queries by query provider 508 or responsive to query responses being provided (as in 406), or at any other time. With reference to execution flow 500 of FIG. 5, processor 304 executes compatibility logic 310 stored in memory 306 to activate/execute compatibility engine 512. Compatibility engine 512 generates indications of communication compatibility based on the query responses (as in 406), and provides the indications as an output 514.

As described herein, indications of communication compatibility may be provided to a remote computer system of a trading partner and/or third-party entity. The indications may be provided in various forms including, without limitation, text-based reports, charts, graphical illustrations, spreadsheets, computer code, files such as communication standard libraries (e.g., augmented enforcement libraries), video, audio, and/or multimedia, and/or the like. The described indications may be stored by a host provider in a memory or displayed for review and further analysis.

As shown in FIG. 5, query provider 508 and compatibility engine 512 may be part of a single component, a prediction engine 516, according to embodiments. In such embodiments, query provider logic 310 and compatibility logic 312 may comprise a single block of logic stored in memory 306.

Figure 6:
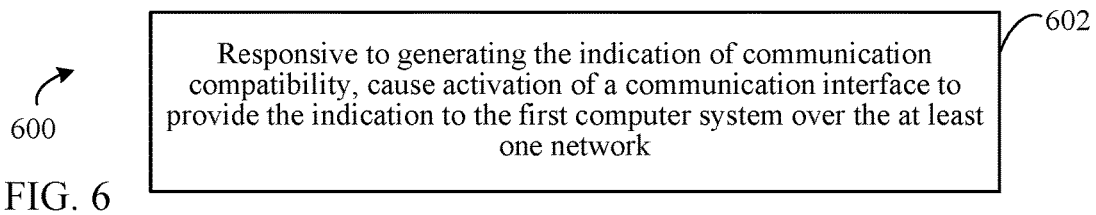
FIG. 6 shows a flowchart of a method for determining communication compatibility between computer systems, according to an example embodiment.

In FIG. 6, a flowchart 600 for determining and providing communication compatibility between computer systems is shown, according to an embodiment. That is, flowchart 600 may exemplify a method performed in a computing system for generating an indication of communication compatibility between a first computer system and one or more second computer systems that are connected to the first computer system via at least one network. In embodiments, flowchart 600 is a further operation of flowchart 400 of FIG. 4. Example techniques and embodiments described herein may be configured and/or implemented to perform various aspects of communication compatibility determination and provision according to flowchart 600. For instance, interoperability system 104 of FIG. 1, interoperability system 204 of FIG. 2, and/or interoperability system 300 of FIG. 3, along with any of their respective subcomponents, may perform functions according to flowchart 600 of FIG. 6. Flowchart 600 is described as follows in the context of interoperability system 300 of FIG. 3 and execution flow 500 of FIG. 5 for exemplary illustration.

Responsive to generating the indication of communication compatibility, activation of a communication interface is caused to provide the indication to the first computer system over the at least one network (602). For example, as noted above, processor 304 is configured to execute compatibility logic 312 to activate/execute compatibility engine 512 which may generate indications of communication compatibility as described herein based at least in part on information in a received declaration from a remote computer system. Because the FHIR standard includes optional or "loose" implementation requirements, the remote computer system is unaware of its communication compatibility status with a host provider and/or other remote computer systems upon transmission/acquisition of the declaration to/by a host provider. For instance, there may me a very large number of remote computer systems (e.g., hundreds or thousands) that wish to exchange messages with each other and with the host provider given the scale and ubiquity of the Internet, but without a notification for indications of communication compatibility, as described herein, verifying compatibility, as well as altering standard/protocol implementations, cannot be quickly and efficiently accomplished. Therefore, according to embodiments, compatibility engine 512 and/or processor 304 are configured to automatically cause the activation of communication interface 302 in order to provide an indication to one of the remote computer systems over a network or communication link, as described herein.

Figure 7:
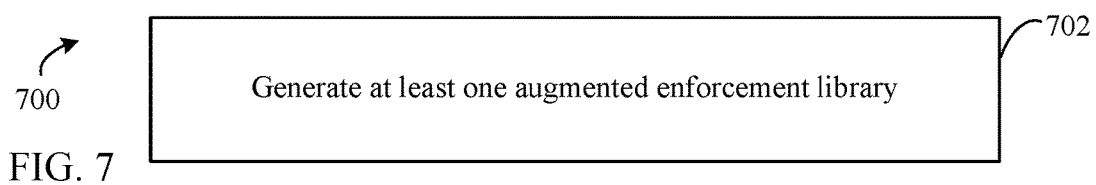
FIG. 7 shows a flowchart of a method for determining communication compatibility between computer systems, according to an example embodiment.

In FIG. 7, a flowchart 700 for determining and providing communication compatibility between computer systems is shown, according to an embodiment. That is, flowchart 700 may exemplify a method performed in a computing system for generating an indication of communication compatibility between a first computer system and one or more second computer systems that are connected to the first computer system via at least one network. In embodiments, flowchart 700 is a further operation of flowchart 400 of FIG. 4, e.g., (408). Example techniques and embodiments described herein may be configured and/or implemented to perform various aspects of communication compatibility determination and provision according to flowchart 700. For instance, interoperability system 104 of FIG. 1, interoperability system 204 of FIG. 2, and/or interoperability system 300 of FIG. 3, along with any of their respective subcomponents, may perform functions according to flowchart 700 of FIG. 7. Flowchart 700 is described as follows in the context of interoperability system 300 of FIG. 3 and execution flow 500 of FIG. 5 for exemplary illustration.

At least one augmented enforcement library is generated (702). For example, as noted above, indications of compatibility may include augmented enforcement libraries that may be implemented by trading partners and third-party entities for communication compatibility and messaging for associated resources. Compatibility logic 312 may be configured to generate one or more augmented enforcement libraries that represent resources in the indications of communication compatibility as described herein (e.g., as in (408)) based at least in part on libraries associated with standard RDF model 314, as well as, information in received declarations. As non-exhaustive examples, augmented enforcement libraries may include changed or additional metadata, definitions, extensions, bindings, and/or, cardinality with respect to implementations of third-party or trading partner standard/protocol implementations, and semantic characteristics.

In embodiments, received declaration information as described herein may also be used to generate augmented enforcement libraries, e.g., Plain Old JavaScript Object (POJO) libraries, Portable Components (POCO) libraries, and/or the like. For instance, differences in standard/protocol implementations that do not affect communication compatibility may be determined by compatibility logic 312. Generated augmented enforcement libraries may include such benign differences as well as enforcement components that mitigate or resolve other differences that do affect communication compatibility.

Accordingly, a host provider as described herein, is configured to provide a core service in which received declarations representative of trading partner implementations of a communication standard/protocol are verified for communication compatibility at, and by, the host provider, as well as, providing indications to trading partners that allow messages and response messages from the host provider to be received and properly consumed by the trading partner.

Figure 8:
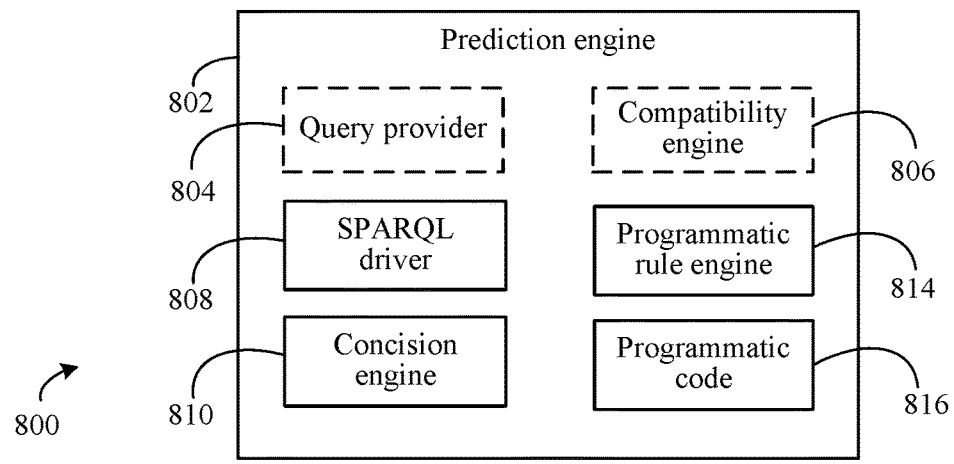
FIG. 8 shows a block diagram of prediction engine components, according to an example embodiment.

In FIG. 8, a block diagram of prediction engine components 800 is shown, according to an embodiment. As noted above with respect to FIG. 5, query provider 508 and compatibility engine 512 may be part of a single component, prediction engine 516, according to embodiments. Prediction engine 802 may be a further embodiment of prediction engine 516. As shown, prediction engine 802 includes a query provider 804 and a compatibility engine 806 that may respectively be further embodiments of query provider 508 and compatibility engine 512 of FIG. 5. For the sake of brevity, in the illustrated embodiment of FIG. 8, query provider 804 and compatibility engine 806 are configured as query provider 508 and compatibility engine 512, with the following additions.

Prediction engine components 800 includes a SPARQL Protocol and RDF Query Language (SPARQL) driver 808, a concision engine 810, a programmatic rule engine 814, and programmatic code 816, although one or more of these components may not be included, or additional components may be added, according to embodiments.

In prediction engine components 800, query provider 804 may include or utilize SPARQL driver 808. SPARQL driver 808 is configured to provide queries against an ontology model, according to embodiments, such as RDF ontology model 316 and/or RDF ontology model 510. SPARQL driver 808 is configured to query both the required branches and the optional branches of graphical models associated with requirements and optional aspects of communication standards/protocols, such as, but not limited to FHIR. In embodiments, SPARQL driver 808 is configured to return not only matched query results, e.g., conjunctions for triples, etc., but is also configured to return query results for unmatched queries, disjunctions, and/or the like.

Prediction engine 802 is configured to utilize concision engine 810 for providing conciseness in data, information, etc., as described herein. Concision engine 810 is configured to remove extraneous and/or unused data and information from one or more of the described embodiments such as, but without limitation, declarations, models, query results, metadata, programmatic code, messages, etc. Concision engine 810 may be configured to perform concision functions according to Plain Old JavaScript Object (POJO) concision, and/or the like, in embodiments.

In prediction engine components 800, compatibility engine 806 may include or utilize one or more of a programmatic rule engine 814 and programmatic code 816 (which may be stored in a memory or storage as described herein). In embodiments, compatibility engine 806 may prompt the execution of programmatic code 816 by a processor to invoke, execute, or activate programmatic rule engine 814. Programmatic rule engine 814 is configured to determine differences between host provider components and trading partner (or third-party entity) components within an ontology model based on query responses, as described herein. The differences may manifest due to implementation variations for metadata, extensions, definitions, constraints, bindings, libraries, semantic characteristics, etc., programmatic rule engine 814 is configured to determine the differences, and also to differentiate between differences that will or may impact communication compatibility and differences that will not impact communication compatibility.

Referring to both FIG. 5 and FIG. 8, it should be noted that in embodiments where query provider 508 and compatibility engine 512 are separate components, query provider 508 may still include one or more of SPARQL driver 808 and/or concision engine 810, and compatibility engine 512 may still include one or more of concision engine 810, programmatic rule engine 814, and/or programmatic code 816.

IV. Example Ontology Model Embodiments

As described above, communication standards/protocols may provide many resources, and information about these resources may be communicated in messaging between entities such as host providers, trading partners, and/or third-party entities. For instance, messaging between computer systems using FHIR may include the exchange of clinical information that may relate to a number of defined resources associated with, but not limited to, patients, practitioners, appointments, clinical observations, clinical documents, medications, accounts, and/or the like, as defined by the FHIR standard. An extensive list of resources for FHIR is not provided here for the sake of brevity, however, it is contemplated that any FHIR resources may be similarly or analogously treated and/or modeled according to the examples described herein.

Modeling based on metadata that defines the structure and properties of FHIR resources in RDF may be performed according to the described techniques and embodiments. The RDF modeling allows the described embodiments to perform targeted challenges against RDF models as these models are structured to provide for versatile, targeted queries. For example, a "Patient" resource for FHIR may be modeled based on its metadata to allow the generation of an RDF model for the resource. The following is an example, non-limiting code segment represented in ".ttl" format, e.g., in a terse RDF triple language ("TTL"), showing a compact text form of a graphical RDF model:

```
# baseURI: http://hostprovider.org/FHIR
@prefix FHIR: <http://hostprovider.org/FHIR#> .
@prefix owl: <http://www.w3.org/2002/07/owl#> .
@prefix rdf: <http://www.w3.org/1999/02/22-rdf-syntax-ns#>
 .
@prefix rdfs: <http://www.w3.org/2000/01/rdf-schema#> .
@prefix xsd: <http://www.w3.org/2001/XMLSchema#> .
<http://hostprovider.org/FHIR>
    rdf:type owl:Ontology ;
    owl:versionInfo "Created with a composer"^^xsd:string ;
.
FHIR:Patient
    rdf:type owl:Class ;
    rdfs:comment "Demographics and other administrative information about an individual or animal receiving care or other health-related services."^^xsd:string ;
    rdfs:subClassOf FHIR:DomainResource ;
    rdfs:subClassOf [
        rdf:type owl:Restriction ;
        owl:maxCardinality "1"^^xsd:nonNegativeInteger ;
        owl:onProperty
<http://hostprovider.org/FHIR#Patient.active> ;
    ] ;
    rdfs:subClassOf [
        rdf:type owl:Restriction ;
        owl:maxCardinality "1"^^xsd:nonNegativeInteger ;
        owl:onProperty
<http://hostprovider.org/FHIR#Patient.animal> ;
    ] ;
    rdfs:subClassOf [
        rdf:type owl:Restriction ;
        owl:maxCardinality "1"^^xsd:nonNegativeInteger ;
        owl:onProperty
<http://hostprovider.org /FHIR#Patient.birthDate> ;
    ] ;
    rdfs:subClassOf [
        rdf:type owl:Restriction ;
        owl:maxCardinality "1"^^xsd:nonNegativeInteger ;
        owl:onProperty
<http://hostprovider.org/FHIR#Patient.deceased> ;
    ] ;
    rdfs:subClassOf [
        rdf:type owl:Restriction ;
```

-continued

```
        owl:maxCardinality "1"^^xsd:nonNegativeInteger ;
        owl:onProperty
<http://hostprovider.org/FHIR#Patient.gender> ;
    ] ;
.
    .
    .
    .
<http://hostprovider.org/FHIR#Patient.Link.type>
    rdf:type owl:DatatypeProperty ;
    FHIR:binding "link-type"^^xsd:string ;
    FHIR:bindingStrength "required"^^xsd:string ;
    rdfs:comment "The type of link between this patient resource and another patient resource."^^xsd:string ;
    rdfs:domain FHIR:PatientLinkComponent ;
    rdfs:range rdf:code ;
.
<http://hostprovider.org/FHIR#Patient.active>
    rdf:type owl:DatatypeProperty ;
    FHIR:isModifier "true"^^xsd:boolean ;
    FHIR:isSummaryItem "true"^^xsd:boolean ;
    rdfs:comment "Whether this patient record is in active use."^^xsd:string ;
    rdfs:domain FHIR:Patient ;
    rdfs:range xsd:boolean ;
.
<http://hostprovider.org/FHIR#Patient.address>
    rdf:type owl:ObjectProperty ;
    FHIR:isSummaryItem "true"^^xsd:boolean ;
    rdfs:comment "Addresses for the individual."^^xsd:string
;
    rdfs:domain FHIR:Patient ;
    rdfs:range FHIR:Address ;
.
<http://hostprovider.org/FHIR#Patient.animal>
    rdf:type owl:ObjectProperty ;
    rdfs:comment "This patient is known to be an animal." ;
    rdfs:domain FHIR:Patient ;
    rdfs:range FHIR:AnimalComponent ;
.
<http://hostprovider.org/FHIR#Patient.birthDate>
    rdf:type owl:DatatypeProperty ;
    FHIR:isSummaryItem "true"^^xsd:boolean ;
    rdfs:comment "The date of birth for the individual."^^xsd:string ;
    rdfs:domain FHIR:Patient ;
    rdfs:range xsd:date ;
.
<http://hostprovider.org/FHIR#Patient.careProvider>
    rdf:type owl:ObjectProperty ;
    rdfs:comment "Patient's nominated care provider."^^xsd:string ;
    rdfs:domain FHIR:Patient ;
    rdfs:range FHIR:Reference ;
.
<http://hostprovider.org/FHIR#Patient.communication>
    rdf:type owl:ObjectProperty ;
    rdfs:comment "Languages that may be used to communicate with the patient about his or her health."^^xsd:string ;
    rdfs:domain FHIR:Patient ;
    rdfs:range FHIR:PatientCommunicationComponent ;
.
<http://hostprovider.org/FHIR#Patient.contact>
    rdf:type owl:ObjectProperty ;
    rdfs:comment "A contact party for the patient."^^xsd:string ;
    rdfs:domain FHIR:Patient ;
    rdfs:range FHIR:ContactComponent ;
.
<http://hostprovider.org/FHIR#Patient.deceased>
    rdf:type owl:DatatypeProperty ;
    FHIR:isModifier "true"^^xsd:boolean ;
    FHIR:isSummaryItem "true"^^xsd:boolean ;
```

-continued

```
    rdfs:comment "Indicates if the individual is deceased or
not."^^xsd:string ;
    rdfs:domain FHIR:Patient ;
    rdfs:range [
        rdf:type owl:Class ;
        owl:oneOf (
            xsd:boolean
            xsd:dateTime
        ) ;
    ] ;
.
<http://hostprovider.org/FHIR#Patient.gender>
    rdf:type owl:DatatypeProperty ;
    FHIR:binding "administrative-gender"^^xsd:string ;
    FHIR:bindingStrength "required"^^xsd:string ;
    FHIR:isSummaryItem "true"^^xsd:boolean ;
    rdfs:comment "The gender that the patient is considered
to have for administration and record keeping
purposes."^^xsd:string ;
    rdfs:domain FHIR:Patient ;
    rdfs:range rdf:code ;
.
<http://hostprovider.org/FHIR#Patient.identifier>
    rdf:type owl:ObjectProperty ;
    FHIR:isSummaryItem "true"^^xsd:boolean ;
    rdfs:comment "An identifier for this
patient."^^xsd:string ;
    rdfs:domain FHIR:Patient ;
    rdfs:range FHIR:Identifier ;
.
<http://hostprovider.org/FHIR#Patient.link>
    rdf:type owl:ObjectProperty ;
    FHIR:isModifier "true"^^xsd:boolean ;
    rdfs:comment "Link to another patient resource that
concerns the same actual patient."^^xsd:string ;
    rdfs:domain FHIR:Patient ;
    rdfs:range FHIR:PatientLinkComponent ;
.
•
•
•
```

The TTL code portion example shown above is illustrative in nature, and is not to be considered limiting. It is contemplated herein that other types of modeling and model representation may be used, as would be understood by a person of skill in the relevant art(s) having the benefit of this disclosure. In embodiments, RDF ontology models may be implemented according to the "OWL" Web Ontology Language (see https://www.w3.org/TR/owl-ref/), and/or their equivalents.

Figure 9:
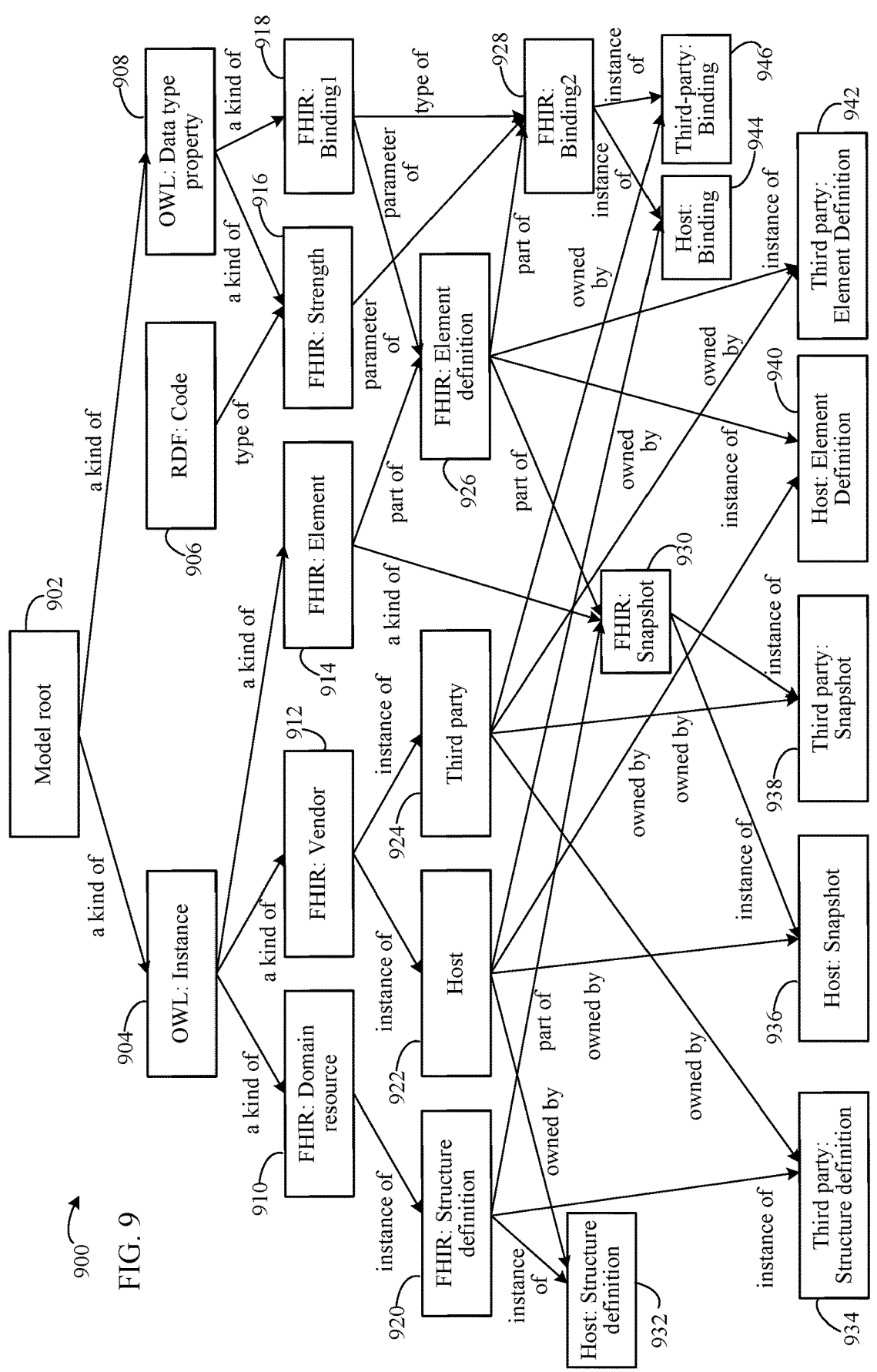
FIG. 9 shows an ontology model, according to an example embodiment.

As noted, interoperability system 104 of FIG. 1, along with further example embodiments thereof, is configured to automatically generating an ontology model (e.g., through RDF) based on information in a declaration(s) from a remote computer system and a standard model of a communication protocol or standard implementation (e.g., FHIR) used by a host provider. The ontology model is a uniform model for any given remote computer system and provides a characterization of how remote computer systems utilize messaging protocols or standards that is based at least in part on a declaration(s) provided by the remote computer system For example, using a formal declaration, a trading partner/third-party entity may invoke an extension to a protocol/standard for messaging, e.g., an extension that is not defined in the protocol/standard, or is optional, that relates to a protocol/standard resource. Using the modeling techniques and embodiments described herein for communication interoperability, the extension may be modeled and analyzed to determine whether or not a communication compatibility issue arises due to the extension being implemented. In embodiments, programmatic code In FIG. 9, an ontology model 900 is shown, according to an embodiment. Ontology model 900 includes a hierarchical structure of dependencies and attributes based on a root instance model root 902. Ontology model 900 is illustrated with respect to OWL according to an embodiment. From model root 902, an OWL: Instance 904 and an OWL: Data type property 908 depend, which have "a kind of" attribute of model root 902. Ontology model 900 also includes RDF: Code 906, e.g., as TTL, which may be generated by a host provider.

From OWL: Instance 904, an FHIR: Domain resource 910, an FHIR: Vendor 912, and an FHIR: Element 914 depend, each of which are "a kind of" OWL: Instance 904. An FHIR: Strength 916 is "a type of From RDF: Code 906 and "a kind of" OWL: Data type property 908, and an FHIR: Binding1 918 is "a kind of" OWL: Data type property 908. An FHIR: Element definition 926 is a "part of" FHIR: Element 914 and a "parameter of" FHIR: Binding1 918. An FHIR: Binding2 928 is a "type of" FHIR: Binding1 918, a "parameter of" FHIR: Strength 916, and a "part of" FHIR: Element definition 926.

An FHIR: Structure definition 920 is an "instance of" FHIR: Domain resource 910, and a Host 922 and a Third party 924 are both an "instance of" FHIR: Vendor 912. A Host: Structure definition 932 is an "instance of" FHIR: Structure definition 920 and is "owned by" Host 922. A Third party: Structure definition 934 is an "instance of" FHIR: Structure definition 920 and is "owned by" Third party 924.

An FHIR: Snapshot 930 is "part of" FHIR: Structure definition 920 and FHIR: Element definition 926, and is "a kind of" FHIR: Element 914. A Host: Snapshot 936 is an "instance of" FHIR: Snapshot 930 and is "owned by" Host 922. A Third party: Snapshot 938 is an "instance of" FHIR: Snapshot 930 and is "owned by" Third party 924.

A Host: Element definition 940 and a Third party: Element Definition 942 are each an "instance of" Element definition 926, and are respectively "owned by" Host 922 and Third party 924. A Host: Binding 944 and a Third party: Binding 946 are each an "instance of" FHIR: Binding2 928, and are respectively "owned by" Host 922 and Third party 924.

In ontology model 900, the "Third party" elements may be generated by a model generator based at least in part on declarations, as described herein, and added to the non-Third party elements (e.g., a standard RDF model based on a host provider and a communication standard/protocol) to create ontology model 900. It should be understood that ontology model 900 may represent a portion of an ontology model in embodiments, but for the sake of brevity and illustrative clarity, only the illustrated portion is described here. In embodiments, ontology model 900 may be queried by a query provider to cause query responses with information relating to differences in communication standard/protocol implementations between the Host and the Third party.

V. Further Example Embodiments and Advantages

As noted above, systems and devices, including interoperability systems, may be configured in various ways to perform communication compatibility functions for messaging according to a communication standard/protocol. For instance, in embodiments, a declaration of a trading partner may be advertised on a remote computer system and may be consumed by a host provider computer system that includes an interoperability system. An ontology model of an implementation of the standard/protocol of the trading partner is generated by the host provider based at least in part on the declaration and a model of the implementation of the host provider. The ontology model may be queried by the host provider to determine differences between the implementations, and indications of communication compatibility can be generated. It is contemplated herein that the techniques and embodiments described are configured to perform one or more of their functions automatically.

The described techniques and embodiments also provide for one or more language exemplars that allow the use of metadata to simplify communication standard/protocol implementations for host provider based declarations so that they are fully baked into the compile time libraries. Exemplars may be characterized in a functional context as a typed convenience wrapper around existing libraries, e.g., FHIR libraries, according to embodiments. This results in less code required for the described interoperability systems, as well as more robust code instances for implementation both at the host provider computer system and third party remote computer systems.

The described techniques and embodiments also provide for increased efficiency in other aspects of achieving interoperability among independent computer systems that share networks and/or communication links. For instance, a trading partner may define and advertise an initial declaration for implementation of a communication standard/protocol that includes only the minimum, required aspects for compliance with the standard/protocol. Once this initial declaration is consumed by a host provider, according to the described techniques and embodiments, the trading partner may use generated indications of communication compatibility from the host provider to drive/develop an actual declaration and implementation for communication compatibility.

Additionally, the ease of use for libraries used in implementations of communication standards/protocols is increased. For example, a formal declaration for an extension of a communication standard/protocol may be modeled, and extensions compatible with host implementations may be included in augmented enforcement libraries.

The described techniques and embodiments may be utilized as or in any computing device or distributed computer system. The described techniques and embodiments provide value and efficiency benefits for large, and still increasing, networks of hosts and trading partners that desire to exchange messages according to communication standards/protocols.

All aspects of a communication standard may be included in declarations, as described herein, while in some embodiments, a subset of information indicative of an implementation of a standard may be included in declarations. That is, according to embodiments, a host provider may be configured to generate an indication of communication compatibility based on an abbreviated standard declaration, or a fully-inclusive declaration.

The embodiments and techniques disclosed herein provide for solutions to a network-/Internet-centric problem of determining and providing communication compatibility between communicatively coupled computer systems that are unaware of how each other computer system implements a communication standard/protocol, such as a communication standard that has optional aspects. That is, optional aspects of a communication standard/protocol may result in communication incompatibilities between computer systems when implementations thereof are not supported by, or are not included by, one or more computer systems, as described herein, for communications such as, but not limited to, messaging and/or clinical messaging. In embodiments, this problem is addressed by retrieving and/or receiving a declaration indicative of a communication standard/protocol implementation of a remote computer system by a host provider to activate one or more functions of an interoperability system. For example, when the declaration is consumed by the host provider, a model generator of the host provider is activated to cause the generation of an ontology model of the declaration. This in turn activates a query provider to cause the generation of queries that are provided against the ontology model to generate, or cause to be provided, query responses indicative of differences between the implementation of the remote computer system and the host provider with respect to the communication standard/protocol. An indication of communication compatibility is then caused to be generated by activating a compatibility engine that generates the indication that may include compatibility factors, e.g., related to extensions and/or augmented enforcement libraries. In embodiments, responsive to generating the indication, activation of a communication interface of the host provider is caused to provide the indication to the remote computer system over a network(s) and/or communication link(s).

That is, according to the described embodiments and techniques, any components of interoperability systems and their functions may be caused to be activated for operation/performance thereof based on other operations, functions, actions, and/or the like, including initialization, completion, and/or performance of the, functions, actions, and/or the like.

In some example embodiments, one or more of the operations of the flowcharts described herein may not be performed. Moreover, operations in addition to or in lieu of the operations of the flowcharts described herein may be performed. Further, in some example embodiments, one or more of the operations of the flowcharts described herein may be performed out of order, in an alternate sequence, or partially (or completely) concurrently with each other or with other operations.

The further example embodiments and advantages described in this Section may be applicable to any embodiments disclosed in this Section or in any other Section of this disclosure.

Embodiments and techniques, including methods, described herein may be performed in various ways such as, but not limited to, being implemented by hardware, or hardware combined with one or both of software and firmware.

VI. Example Processing Device Implementations

Interoperability system and device embodiments described herein, such as interoperability system 104 of FIG. 1, along with any respective components/subcomponents and/or further embodiments thereof, and/or any flowcharts, further systems, sub-systems, and/or components, disclosed herein may be implemented in hardware (e.g., hardware logic/electrical circuitry), or any combination of hardware with one or both of software (computer program code or instructions configured to be executed in one or more processors or processing devices) and firmware. In embodiments with respect to the example computer implementations in this Section, main memory, memory cards and memory sticks, memory devices, and/or the like may include and or implement the described techniques and embodiments.

Figure 10:
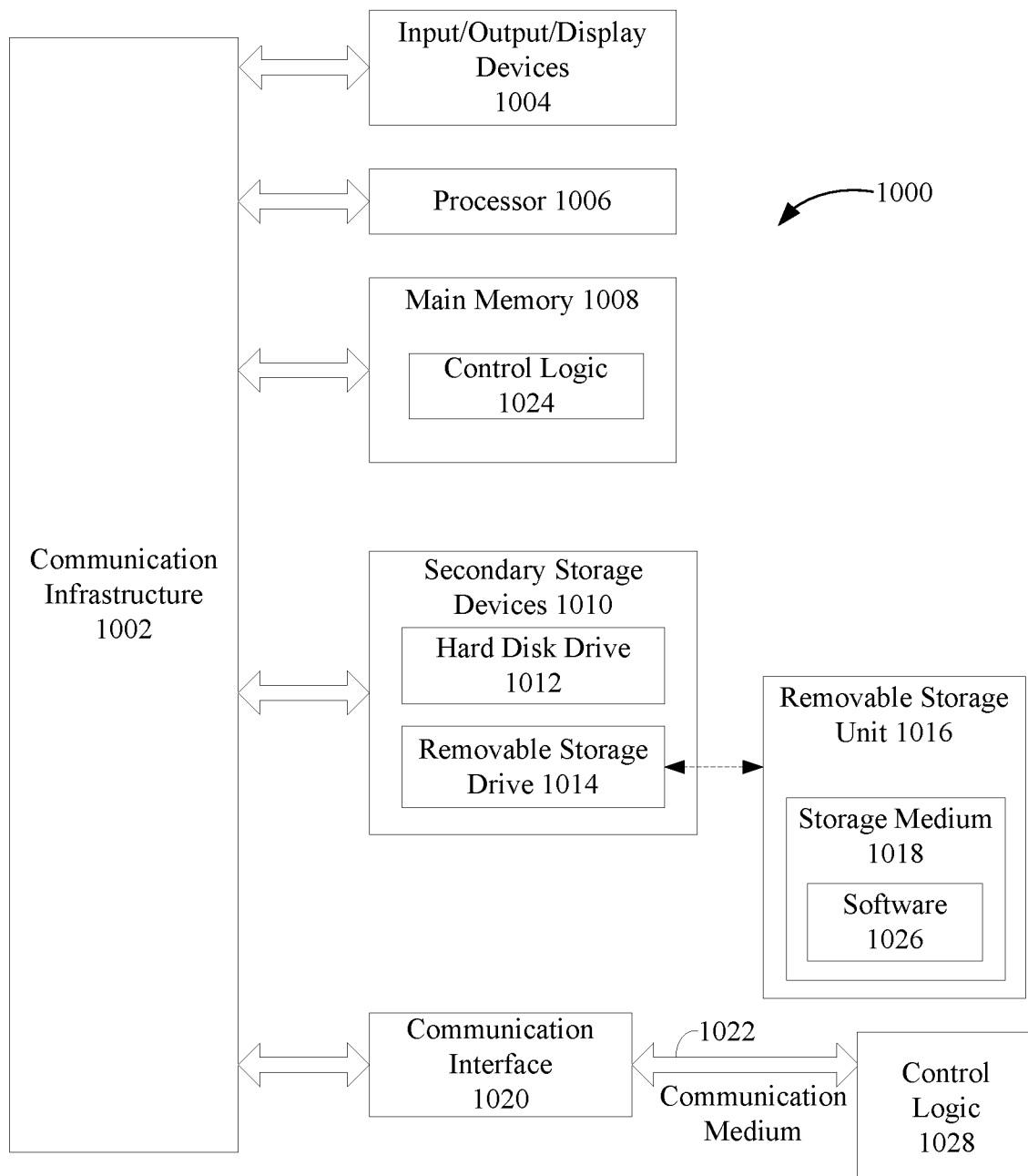
FIG. 10 shows a block diagram of a processing device/system in which the techniques disclosed herein may be performed and the embodiments herein may be utilized.

The embodiments described herein, including devices, systems, methods/processes, and/or apparatuses, may be implemented in or using processing devices, communication systems, servers, and/or, computers, such as a processing device 1000 shown in FIG. 10. It should be noted that processing device 1000 may represent mobile devices, communication devices/systems, entertainment systems/devices, processing devices, and/or traditional computers in one or more embodiments. For example, a interoperability system as described herein, and any of the sub-systems and/or components respectively contained therein and/or associated therewith, along with further embodiments thereof, may be implemented in or using one or more processing devices 1000 and/or similar computing devices.

Processing device 1000 can be any commercially available and well known communication device, processing device, and/or computer capable of performing the functions described herein, such as devices/computers available from International Business Machines®, Apple®, Sun®, HP®, Dell®, Cray®, Samsung®, Nokia®, etc. Processing device 1000 may be any type of computer, including a desktop computer, a server, etc., and may be a computing device or system within another device or system.

Processing device 1000 includes one or more processors (also called central processing units, or CPUs), such as a processor 1006. Processor 1006 is connected to a communication infrastructure 1002, such as a communication bus. In some embodiments, processor 1006 can simultaneously operate multiple computing threads, and in some embodiments, processor 1006 may comprise one or more processors.

Processing device 1000 also includes a primary or main memory 1008, such as random access memory (RAM). Main memory 1008 has stored therein control logic 1024 (computer software), and data.

Processing device 1000 also includes one or more secondary storage devices 1010. Secondary storage devices 1010 include, for example, a hard disk drive 1012 and/or a removable storage device or drive 1014, as well as other types of storage devices, such as memory cards and memory sticks. For instance, processing device 1000 may include an industry standard interface, such a universal serial bus (USB) interface for interfacing with devices such as a memory stick. Removable storage drive 1014 represents a floppy disk drive, a magnetic tape drive, a compact disk drive, an optical storage device, tape backup, etc.

Removable storage drive 1014 interacts with a removable storage unit 1016. Removable storage unit 1016 includes a computer useable or readable storage medium 1018 having stored therein computer software 1026 (control logic) and/or data. Removable storage unit 1016 represents a floppy disk, magnetic tape, compact disk, DVD, optical storage disk, or any other computer data storage device. Removable storage drive 1014 reads from and/or writes to removable storage unit 1016 in a well-known manner.

Processing device 1000 also includes input/output/display devices 1004, such as touchscreens, LED and LCD displays, monitors, keyboards, pointing devices, etc.

Processing device 1000 further includes a communication or network interface 1020. Communication interface 1020 enables processing device 1000 to communicate with remote devices. For example, communication interface 1020 allows processing device 1000 to communicate over communication networks or mediums 1022 (representing a form of a computer useable or readable medium), such as LANs, WANs, the Internet, etc. Network interface 1020 may interface with remote sites or networks via wired or wireless connections.

Control logic 1028 may be transmitted to and from processing device 1000 via the communication medium 1022.

Any apparatus or manufacture comprising a computer useable or readable medium having control logic (software) stored therein is referred to herein as a computer program product or program storage device. This includes, but is not limited to, processing device 1000, main memory 1008, secondary storage devices 1010, and removable storage unit 1016. Such computer program products, having control logic stored therein that, when executed by one or more data processing devices, cause such data processing devices to operate as described herein, represent embodiments.

Techniques, including methods, and embodiments described herein may be implemented by hardware (digital and/or analog) or a combination of hardware with one or both of software and/or firmware. Techniques described herein may be implemented by one or more components. Embodiments may comprise computer program products comprising logic (e.g., in the form of program code or software as well as firmware) stored on any computer useable medium, which may be integrated in or separate from other components. Such program code, when executed by one or more processor circuits, causes a device to operate as described herein. Devices in which embodiments may be implemented may include storage, such as storage drives, memory devices, and further types of physical hardware computer-readable storage media. Examples of such computer-readable storage media include, a hard disk, a removable magnetic disk, a removable optical disk, flash memory cards, digital video disks, random access memories (RAMs), read only memories (ROM), and other types of physical hardware storage media. In greater detail, examples of such computer-readable storage media include, but are not limited to, a hard disk associated with a hard disk drive, a removable magnetic disk, a removable optical disk (e.g., CDROMs, DVDs, etc.), zip disks, tapes, magnetic storage devices, MEMS (micro-electromechanical systems) storage, nanotechnology-based storage devices, flash memory cards, digital video discs, RAM devices, ROM devices, and further types of physical hardware storage media. Such computer-readable storage media may, for example, store computer program logic, e.g., program modules, comprising computer executable instructions that, when executed by one or more processor circuits, provide and/or maintain one or more aspects of functionality described herein with reference to the figures, as well as any and all components, capabilities, and functions therein and/or further embodiments described herein.

Such computer-readable storage media are distinguished from and non-overlapping with communication media (do not include communication media). Communication media embodies computer-readable instructions, data structures, program modules or other data in a modulated data signal such as a carrier wave. The term "modulated data signal" means a signal that has one or more of its characteristics set or changed in such a manner as to encode information in the signal. By way of example, and not limitation, communication media includes wireless media such as acoustic, RF, infrared and other wireless media, as well as wired media and signals transmitted over wired media. Embodiments are also directed to such communication media.

The techniques and embodiments described herein may be implemented as, or in, various types of circuits, devices, apparatuses, and systems. For instance, embodiments may be included, without limitation, in processing devices (e.g., illustrated in FIG. 10) such as computers and servers, as well as communication systems such as switches, routers, gateways, and/or the like, communication devices such as smart phones, home electronics, gaming consoles, entertainment devices/systems, etc. A device, as defined herein, is a machine or manufacture as defined by 35 U.S.C. § 101. That is, as used herein, the term "device" refers to a machine or other tangible, manufactured object and excludes software and signals. Devices may include digital circuits, analog circuits, or a combination thereof. Devices may include one or more processor circuits (e.g., central processing units (CPUs), processor 1006 of FIG. 10), microprocessors, digital signal processors (DSPs), and further types of physical hardware processor circuits) and/or may be implemented with any semiconductor technology in a semiconductor material, including one or more of a Bipolar Junction Transistor (BJT), a heteroj unction bipolar transistor (HBT), a metal oxide field effect transistor (MOSFET) device, a metal semiconductor field effect transistor (MESFET) or other transconductor or transistor technology device. Such devices may use the same or alternative configurations other than the configuration illustrated in embodiments presented herein.

VII. Conclusion

While various embodiments have been described above, it should be understood that they have been presented by way of example only, and not limitation. It will be apparent to persons skilled in the relevant art that various changes in form and detail can be made therein without departing from the spirit and scope of the embodiments. Thus, the breadth and scope of the embodiments should not be limited by any of the above-described exemplary embodiments, but should be defined only in accordance with the following claims and their equivalents.

What is claimed is:

1. An interoperability system for generating an indication of communication compatibility between a first computer system and one or more second computer systems that are connected to the first computer system via at least one network, comprising:
   a memory configured to store program instructions; and
   at least one processor configured to execute the program instructions to perform a method comprising:
      receiving at least one declaration structured in accordance with a first implementation of a communication protocol from the first computer system over the at least one network;
      activating a model generator responsive to receiving the at least one declaration and generating an ontology model by the model generator that is representative of characteristics of the first implementation of the communication protocol used by the first computer system based on the at least one declaration;
      activating a query provider, generating at least one query by the query provider, and applying the at least one query against the ontology model that causes at least one query response to be provided, the at least one query response indicating one or more of resource representations or data structures of the first implementation of the communication protocol that are accepted by a second implementation of the communication protocol and another one or more of the resource representations or the data structures of the first implementation of the communication protocol that are not accepted by the second implementation of the communication protocol; and
      generating the indication of communication compatibility based on the at least one query response, the indication of communication compatibility including a set of incompatibility factors, based on the other one or more of the resource representations or the data structures of the first implementation that are not accepted, that represent one or more differences between the first implementation of the communication protocol and the second implementation of the communication protocol that prevent communication compatibility between the first computer system and the one or more second computer systems.

2. The interoperability system of claim 1, the method further comprising:
   responsive to generating the indication of communication compatibility, causing activation of a communication interface to provide the indication to the first computer system over the at least one network.

3. The interoperability system of claim 1, wherein the communication protocol is FHIR (Fast Healthcare Interoperability Resources).

4. The interoperability system of claim 3, wherein generating the indication comprises one or more of:
   generating at least one augmented enforcement library associated with the FHIR protocol;
   generating computer code; and
   generating at least one of a text-based report, a chart, a graphical illustration, or a spreadsheet.

5. The interoperability system of claim 3, wherein the set of incompatibility factors comprises one or more extension factors indicative of extension implementation in the at least one declaration.

6. The interoperability system of claim 1, wherein the ontology model comprises a resource description framework (RDF) model.

7. The interoperability system of claim 1, wherein the declaration structure comprises at least one of metadata, extensions, definitions, bindings, cardinality, and semantic characteristics of information.

8. The interoperability system of claim 1, wherein the interoperability system:
   is included in the one or more second computer systems; or
   is included in a cloud-based computer system.

9. A method for generating an indication of communication compatibility between a first computer system and one or more second computer systems that are connected to the first computer system via at least one network, the method comprising:
   receiving at least one declaration structured in accordance with a first implementation of a communication protocol from the first computer system over the at least one network;
   activating a model generator responsive to receiving the at least one declaration and generating an ontology model by the model generator that is representative of characteristics of the first implementation of the communication protocol used by the first computer system based on the at least one declaration;
   activating a query provider, generating at least one query by the query provider, and applying the at least one query against the ontology model that causes at least one query response to be provided, the at least one query response indicating one or more of resource representations or data structures of the first implementation of the communication protocol that are accepted by a second implementation of the communication protocol and another one or more of the resource representations or the data structures of the first implementation of the communication protocol that are not accepted by the second implementation of the communication protocol; and generating the indication of communication compatibility based on the at least one query response, the indication of communication compatibility including a set of incompatibility factors, based on the other one or more of the resource representations or the data structures of the first implementation that are not accepted, that represent one or more differences between the first implementation of the communication protocol and the second implementation of the communication protocol that prevent communication compatibility between the first computer system and the one or more second computer systems.

10. The method of claim 9, wherein the communication protocol is FHIR (Fast Healthcare Interoperability Resources).

11. The method of claim 10, wherein generating the indication comprises one or more of:
generating at least one augmented enforcement library associated with the FHIR protocol;
generating computer code; and
generating at least one of a text-based report, a chart, a graphical illustration, or a spreadsheet.

12. The method of claim 10, wherein the set of incompatibility factors comprises one or more extension factors indicative of extension implementation in the at least one declaration.

13. The method of claim 9, wherein the ontology model comprises a resource description framework (RDF) model.

14. The method of claim 9, wherein the declaration structure comprises at least one of metadata, extensions, definitions, bindings, cardinality, and semantic characteristics of information.

15. The method of claim 9, wherein the method is performed by an interoperability system that is included in the one or more second computer systems, or is included in a cloud-based computer system.

16. A non-transitory computer readable storage medium encoded with program instructions that, when executed by a computing device, cause the computing device to perform a method for generating an indication of communication compatibility between a first computer system and one or more second computer systems that are connected to the first computer system via at least one network, the program instructions comprising: model generator logic that is activated responsive to receiving at least one declaration structured in accordance with a first implementation of a communication protocol from the first computer system over the at least one network and that generates an ontology model that is representative of characteristics of the first implementation of the communication protocol used by the first computer system based on the at least one declaration; query provider logic, that is activated responsive to generation of the ontology model, that generates at least one query and applies the at least one query against the ontology model that causes at least one query response to be provided, the at least one query response indicating one or more of resource representations or data structures of the first implementation of the communication protocol that are accepted a second implementation of the communication protocol and another one or more of the resource representations or the data structures of the first implementation of the communication protocol that are not accepted by the second implementation of the communication protocol; and compatibility logic to generate the indication of communication compatibility between the first computer system and the one or more second computer systems based on the at least one query response, the indication of communication compatibility including a set of incompatibility factors, based on the other one or more of the resource representations or the data structures of the first implementation that are not accepted, that represent one or more differences between the first implementation of the communication protocol and the second implementation of the communication protocol that prevent communication compatibility between the first computer system and the one or more second computer systems.

17. The non-transitory computer readable storage medium of 16, wherein the set of incompatibility factors comprises one or more extension factors indicative of extension implementation in the at least one declaration.

18. The non-transitory computer readable storage medium of 16, wherein the communication protocol is FHIR (Fast Healthcare Interoperability Resources).

19. The non-transitory computer readable storage medium of 16, wherein the ontology model comprises a resource description framework (RDF) model.

20. The non-transitory computer readable storage medium of 16, wherein the compatibility logic, to generate the indication of communication compatibility, generates one or more of: at least one augmented enforcement library associated with the FHIR protocol; computer code; and at least one of a text-based report, a chart, a graphical illustration, or a spreadsheet.

* * * * *

UNITED STATES PATENT AND TRADEMARK OFFICE
CERTIFICATE OF CORRECTION

PATENT NO. : 10,964,430 B2  
APPLICATION NO. : 15/153147  
DATED : March 30, 2021  
INVENTOR(S) : Keith Willard et al.

Page 1 of 1

It is certified that error appears in the above-identified patent and that said Letters Patent is hereby corrected as shown below:

In the Claims

In Column 28, Line 35, in Claim 17, delete "16," and insert -- claim 16, --, therefor.

In Column 28, Line 39, in Claim 18, delete "16," and insert -- claim 16, --, therefor.

In Column 28, Line 42, in Claim 19, delete "16," and insert -- claim 16, --, therefor.

In Column 28, Line 44, in Claim 20, delete "16," and insert -- claim 16, --, therefor.

Signed and Sealed this  
Thirteenth Day of July, 2021

Drew Hirshfeld  
*Performing the Functions and Duties of the*  
*Under Secretary of Commerce for Intellectual Property and*  
*Director of the United States Patent and Trademark Office*